US007901926B2

(12) United States Patent
Yu et al.

(10) Patent No.: US 7,901,926 B2
(45) Date of Patent: Mar. 8, 2011

(54) LACTOBACILLUS ISOLATES HAVING ANTI-INFLAMMATORY ACTIVITIES AND USES OF THE SAME

(75) Inventors: Tu-Wen Yu, Shanhua Township, Tainan County (TW); Jun-Sheng Li, Shanhua Township, Tainan County (TW); Feng-Ching Hsieh, Shanhua Township, Tainan County (TW); Ching-Pei Chen, Shanhua Township, Tainan County (TW); Tsuei-Yin Huang, Shanhua Township, Tainan County (TW); Ying-Chen Lu, Shanhua Township, Tainan County (TW)

(73) Assignee: GenMont Biotech Incorporation, Shanhua Township, Tainan County (TW)

( * ) Notice: Subject to any disclaimer, the term of this patent is extended or adjusted under 35 U.S.C. 154(b) by 0 days.

(21) Appl. No.: 12/340,081

(22) Filed: Dec. 19, 2008

(65) Prior Publication Data

US 2009/0274672 A1 Nov. 5, 2009

(30) Foreign Application Priority Data

Apr. 30, 2008 (TW) .............................. 97115882 A

(51) Int. Cl.
*A01N 63/00* (2006.01)
*C12N 1/20* (2006.01)
(52) U.S. Cl. .................. 435/252.9; 424/93.45; 435/853
(58) Field of Classification Search .................. None
See application file for complete search history.

(56) References Cited

U.S. PATENT DOCUMENTS

2002/0176910 A1* 11/2002 Raczek ........................ 426/61

OTHER PUBLICATIONS

Yasuhiro Kameyama, et al., Bone response to mechanical loading in adult rats with collagen-induced arthritis, Bone, 2004, pp. 948-956, vol. 35.

Jae-Seon So, et al., *Lactobacillus casei* suppresses experimental arthritis by down-regulating T helper 1 effector functions, Molecular Immunology, 2008, pp. 1-10.
Gabriela Garcia, et al., Suppression of Collagen-induced Arthritis by Oral or Nasal Administration of Type II Collagen, Journal of Autoimmunity, 1999, vol. 13, pp. 315-324.
Marc Feldmann, Role of Cytokines in Rheumatoid Arthritism, Annu. Rev. Immunol, 1996, vol. 14, pp. 397-440.
Aymerich, et al., *Bacteriocin-producing lactobacilli in Spanish-style fermented sausages: characterization of bacteriocins*, Food Microbiology, 2000, 17, 33-35.
Tichaczek, et al. *Cloning and sequencing of sakP encoding sakacin P, the bacteriocin produced by Lactobacillus sake LTH 673*, Microbiology (1994), 140, 361-367.
Jones, et al. *Inhibition by Lactobacillus sakei of other species in the flora of vacuum packaged raw meats during prolonged storage*, Food Microbiology 26 (2009) 876-881.
Kawai, et al. *Lactobacillus reuteri LA6 and Lactobacillus gasseri LA39 isolated from faeces of the same human infant produce identical cyclic bacteriocin*, Food Microbiology, 2001, 18, 407-415.
Hammes, et al. *New Developments in Meat Starter Cultures*, Meat Science, vol. 49, No. Suppl. 1, S125-S138, 1998.

* cited by examiner

*Primary Examiner* — David M Naff
*Assistant Examiner* — Deborah K. Ware
(74) *Attorney, Agent, or Firm* — Sunstein Kann Murphy & Timbers LLP

(57) ABSTRACT

Disclosed herein are two *Lactobacillus* isolates having anti-inflammatory activities and beneficial probiotic properties, i.e., *Lactobacillus sakei* GMNL-76 and *Lactobacillus reuteri* GMNL-89, which were deposited in the Biosource Collection and Research Center (BCRC) of the Food Industry Research and Development Institute (FIRDI) under accession numbers BCRC 910355 and BCRC 910340 and in the China Center for Type Culture Collection (CCTCC) under accession numbers CCTCC M 207153 and CCTCC M 207154, respectively. The two *Lactobacillus* isolates and their sub-cultured offspring can be used in the preparation of a variety of food products, and in the manufacture of pharmaceutical compositions for treating and/or alleviating diseases associated with inflammation, such as rheumatoid arthritis.

8 Claims, 6 Drawing Sheets

GGGGGGGGGT GCTATACATG CAAGTCGAAC GCACTCTCGT TTAGATTGAA
GGAGCTTGCT CCTGATTGAT AAACATTTGA GTGAGTGGCG GACGGGTGAG
TAACACGTGG GTAACCTGCC CTAAAGTGGG GGATAACATT TGGAAACAGA
TGCTAATACC GCATAAAACC TAACACCGCA TGGTGTAGGG TTGAAAGATG
GTTTCGGCTA TCACTTTAGG ATGGACCCGC GGTGCATTAG TTAGTTGGTG
AGGTAAAGGC TCACCAAGAC CGTGATGCAT AGCCGACCTG AGAGGGTAAT
CGGCCACACT GGGACTGAGA CACGGCCCAG ACTCCTACGG GAGGCAGCAG
TAGGGAATCT TCCACAATGG ACGAAAGTCT GATGGAGCAA CGCCGCGTGA
GTGAAGAAGG TTTTCGGATC GTAAAACTCT GTTGTTGGAG AAGAATGTAT
CTGATAGTAA CTGATCAGGT AGTGACGGTA TCCAACCAGA AAGCCACGGC
TAACTACGTG CCAGCAGCCG GGGTAATAC TAAAA

FIG. 4

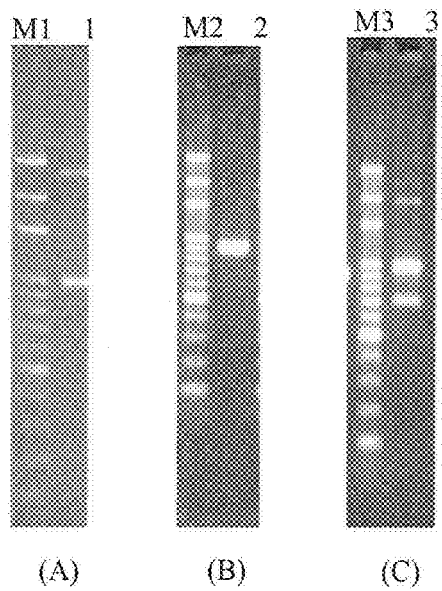

FIG. 5

GGCTTGGGAT ACCGTCACTG CGTGAACAGT TACTCTCACG CACGTTCTTC
TCCAACAACA GAGCTTTACG AGCCGAAACC CTTCTTCACT CACGCGGTGT
TGCTCCATCA GGCTTGCGCC CATTGTGGAA GATTCCCTAC TGCTGCCTCC
CGTAGGAGTA TGGACCGTGT CTCAGTTCCA TTGTGGCCGA TCAGTCTCTC
AACTCGGCTA TGCATCATCG CCTTGGTAAG CCGTTACCTT ACCAACTAGC
TAATGCACCG CAGGTCCATC CCAGAGTGAT AGCCAAAGCC ATCTTTCAAA
CAAAAGCCAT GTGGCTTTTG TTGTTATGCG GTATTAGCAT CTGTTTCCAA
ATGTTATCCC CCGCTCCGGG GCAGGTTACC TACGTGTTAC TCACCCGTCC
GCCACTCACT GGTGATCCAT CGTCAATCAG GTGCAAGCAC CATCAATCAG
TTGGGCCAGT GCGTACGACT TGCATGTATT AGGCACACCG CCGGCGTTCA
TCCTGAGCCA GAACGAACTC TC

FIG. 6

SEQUENCE LISTING

```
<160> NUMBER OF SEQ ID NOS: 5

<210> SEQ ID NO 1
<211> LENGTH: 20
<212> TYPE: DNA
<213> ORGANISM: artificial
<220> FEATURE:
<223> OTHER INFORMATION: PAF primer for PCR amplification of 16S rDNA
      of Lactobacillus

<400> SEQUENCE: 1
agagtttgat cctggctcag                                              20

<210> SEQ ID NO 2
<211> LENGTH: 18
<212> TYPE: DNA
<213> ORGANISM: artificial
<220> FEATURE:
<223> OTHER INFORMATION: 536R primer for PCR amplification of 16S
      rDNA of Lactobacillus
```

-continued

<400> SEQUENCE: 2
gtattaccgc ggctgctg                                                      18

<210> SEQ ID NO 3
<211> LENGTH: 10
<212> TYPE: DNA
<213> ORGANISM: artificial
<220> FEATURE:
<223> OTHER INFORMATION: 10-mer primer for PCR amplification of gene
      of Lactobacillus

<400> SEQUENCE: 3
atgtaacgcc                                                               10

<210> SEQ ID NO 4
<211> LENGTH: 535
<212> TYPE: DNA
<213> ORGANISM: Lactobacillus sakei GMNL-76

<400> SEQUENCE: 4
gggggggggt gctatacatg caagtcgaac gcactctcgt ttagattgaa ggagcttgct         60
cctgattgat aaacatttga gtgagtggcg acgggtgag taacacgtgg gtaacctgcc        120
ctaaagtggg ggataacatt tggaaacaga tgctaatacc gcataaaacc taacaccgca       180
tggtgtaggg ttgaaagatg gtttcggcta tcactttagg atggacccgc ggtgcattag       240
ttagttggtg aggtaaaggc tcaccaagac cgtgatgcat agccgacctg agagggtaat       300
cggccacact gggactgaga cacggcccag actcctacgg gaggcagcag tagggaatct       360
tccacaatgg acgaaagtct gatggagcaa cgccgcgtga gtgaagaagg ttttcggatc       420
gtaaaactct gttgttggag aagaatgtat ctgatagtaa ctgatcaggt agtgacggta       480
tccaaccaga aagccacggc taactacgtg ccagcagccg ggggtaatac taaaa           535

<210> SEQ ID NO 5
<211> LENGTH: 522
<212> TYPE: DNA
<213> ORGANISM: Lactobacillus reuteri GMNL-89

<400> SEQUENCE: 5
ggcttgggat accgtcactg cgtgaacagt tactctcacg cacgttcttc tccaacaaca        60
gagctttacg agccgaaacc cttcttcact cacgcggtgt tgctccatca ggcttgcgcc       120
cattgtggaa gattccctac tgctgcctcc cgtaggagta tggaccgtgt ctcagttcca       180
ttgtggccga tcagtctctc aactcggcta tgcatcatcg ccttggtaag ccgttacctt       240
accaactagc taatgcaccg caggtccatc ccagagtgat agccaaagcc atctttcaaa       300
caaaagccat gtggcttttg ttgttatgcg gtattagcat ctgtttccaa atgttatccc       360
ccgctcgggg caggttacc tacgtgttac tcacccgtcc gccactcact ggtgatccat       420
cgtcaatcag gtgcaagcac catcaatcag ttgggccagt cgtacgact tgcatgtatt       480 aggcacaccg ccggcgttca tcctgagcca gaacgaactc tc                         522

LACTOBACILLUS ISOLATES HAVING ANTI-INFLAMMATORY ACTIVITIES AND USES OF THE SAME

CROSS-REFERENCE TO RELATED APPLICATION

This application claims priority of Taiwanese application no. 097115882, filed on Apr. 30, 2008.

BACKGROUND OF THE INVENTION

1. Field of the Invention

The invention relates to two *Lactobacillus* isolates having anti-inflammatory activities and beneficial probiotic properties, namely *Lactobacillus sakei* GMNL-76 and *Lactobacillus reuteri* GMNL-89, which were deposited in the Biosource Collection and Research Center (BCRC) of the Food Industry Research and Development Institute (FIRDI) under accession numbers BCRC 910355 and BCRC 910340, respectively, and in the China Center for Type Culture collection (CCTCC) under accession numbers CCTCC M 207153 and CCTCC M 207154, respectively. The two isolates and their sub-cultured offspring can be used in the preparation of a variety of food products, and in the manufacture of pharmaceutical compositions for treating and/or alleviating diseases associated with inflammation, such as rheumatoid arthritis.

2. Description of the Related Art

Cytokines are known to be involved in numerous important biological processes, including inflammation, tissue repair, cell growth, fibrosis, angiogenesis, and immune response. Therefore, cytokines play an important role in autoimmune diseases.

M. Feldmann et al. investigated the pathogenesis of rheumatoid arthritis by analyzing cytokine expression and regulation in rheumatoid arthritis synovial tissue (M. Feldmann et al. (1996), *Annu. Rev. Immunol.*, 14:397-440). According to M. Feldmann et al., cytokines are divided into four main classes: (1) proinflammatory cytokines; (2) immunoregulatory cytokines; (3) chemotactic cytokines; and (4) mitogenic cytokines.

Proinflammatory cytokines are a group of molecules produced by T-helper 1 cells (Th1 cells for short) and having the ability to regulate delayed-type hypersensitivity reaction, including interleukin-1 (IL-1), interferon-γ (IFN-γ), tumor necrosis factor-α (TNF-α), and granulocyte-macrophage colony stimulating factor (GM-CSF). Cartilage destruction observed in rheumatic diseases has been widely recognized to have been caused by activity of matrix metalloproteinases (MMPs). MMPs are generated by activated macrophages and fibroblasts that are responsive to proinflammatory cytokines (such as IL-1 or TNF-α). M. Feldmann et al. further reported that injection of IL-1 or TNF-α into collagen-immunized mice or rats, or local injection of IFN-γ into footpads of collagen type II-immunized mice would promote the incidence of rheumatoid arthritis and exacerbates the disease (M. Feldmann et al. (1996), supra).

Immunoregulatory cytokines (also referred to as anti-inflammatory cytokines) are a group of molecules generated by T-helper 2 cells (Th2 cells for short) and having the ability to inhibit inflammatory reaction, including IL-4, IL-10, IL-13, and Transforming Growth Factor-β (TGF-β). In an article by G. Garcia et al. (G. Garcia et al. (1999), *Journal of Autoimmunity*, 13:315-324), it is reported that the two immunoregulatory cytokines, TGF-β and IL-10, not only inhibit production of proinflammatory cytokines that will induce MMPs, they will also induce production of natural inhibitors of MMPs (i.e., tissue inhibitors of matrix metalloproteinases, TIMPs). G. Garcia et al. further pointed out that IL-10 was known to have the ability to inhibit production of IFN-γ from Th1 cells and production of a variety of cytokines from other leukocyte populations. IL-10 inhibited production of IL-1, IL-6, TNF-α, and IL-8 and G-CSF (granulocyte-colony stimulating factor) from macrophages, and production of IL-1, TNF, IL-8, macrophage inflammatory protein 1α (MIP1α), and macrophage inflammatory protein 1β (MIP1β) from polymorphonuclear cells. Most of these cytokines and chemokines are associated with the pathological process of rheumatoid arthritis (G. Garcia et al. (1999), supra).

These study results reveal that proinflammatory cytokines (such as TNF-α and IFN-γ) associated with Th1 cells promote inflammation and aggravate rheumatoid arthritis, whereas immunoregulatory cytokines (such as IL-10 and IL-4) associated with Th2 cells can not only inhibit production of proinflammatory cytokines but also induce production of TIMPs to thereby reduce cartilage destruction.

Jae-Seon So reported that oral administration of *Lactobacillus casei* suppressed collagen-induced arthritis (CIA) and reduced paw swelling, lymphocyte infiltration, and destruction of cartilage tissue. *Lactobacillus casei* administration reduced type II collagen (CII)-reactive proinflammatory molecules (IL-1β, IL-2, IL-6, IL-12, IL-17, IFN-γ, TNF-α, and Cox-2) by CD4+ T cells. *Lactobacillus casei* administration also reduced translocation of NF-κB into nucleus and CII-reactive Th1-type IgG isotypes IgG2a and IgG2b, while up-regulating IL-10 levels (Jae-Seon So et al. (2008), *Mol. Immunol.*, 45(9):2690-2699; Epub Feb. 19, 2008).

If rheumatoid arthritis can be treated/alleviated through administration of *Lactobacillus* isolates, a safe and inexpensive drug might be developed for patients with rheumatoid arthritis.

To achieve the aforesaid objective, the Applicants have screened two *Lactobacillus* isolates from gastrointestinal tract specimens of adult subjects from Taiwan. The two *Lactobacillus* isolates are phylogenetically different from known strains of their respective species, and possess anti-inflammatory activities that can stimulate generation of large amounts of IL-10 and relatively small amounts of IFN-γ and/or TNF-α. Therefore, these *Lactobacillus* isolates are anticipated to be useful in treating diseases associated with inflammation, including, but not limited to, rheumatoid arthritis.

SUMMARY OF THE INVENTION

Accordingly, in a first aspect, the present invention provides an isolated strain of *Lactobacillus* sp. having anti-inflammatory activity, wherein the isolated strain is (i) a deposited strain selected from:
(a) *Lactobacillus sakei* GMNL-76 deposited in the Biosource Collection and Research Center (BCRC) of the Food Industry Research and Development Institute (FIRDI) under an accession number BCRC 910355 and in the China Center for Type Culture Collection (CCTCC) under an accession number CCTCC M 207153; and
(b) *Lactobacillus reuteri* GMNL-89 deposited in the Biosource Collection and Research Center (BCRC) of the Food Industry Research and Development Institute (FIRDI) under an accession number BCRC 910340 and in the China Center for Type Culture Collection (CCTCC) under an accession number CCTCC M 207154; or
(ii) a subcultured offspring of the deposited strain (i).

In a second aspect, the present invention provides a food product comprising an edible material and the isolated strain of *Lactobacillus* sp. according to the present invention.

In a third aspect, the present invention provides a pharmaceutical composition having anti-inflammatory activity, which comprises the isolated strain of *Lactobacillus* sp. according to the present invention.

In a fourth aspect, the present invention provides a method for treating an inflammation-associated disease in a subject, including administering the isolated strain of *Lactobacillus* sp. according to the present invention to the subject in need of the treatment.

BRIEF DESCRIPTION OF THE DRAWINGS

Other features and advantages of the present invention will become apparent in the following detailed description of the preferred embodiment with reference to the accompanying drawings, of which:

FIG. 4 illustrates a 16S rDNA nucleotide sequence (SEQ ID NO: 4) of *Lactobacillus* GMNL-76;

FIG. 5 shows photographic image results of electrophoresis on 1.8% agarose gel which was performed subsequent to a Random Amplified Polymorphic DNA (RAPD) analysis conducted using genomic DNAs of *Lactobacillus* GMNL-76 according to this invention and of two known strains of *Lactobacillus sakei*, BCRC 12933 and BCRC 17500, as templates and using Lac P2 primer(s), wherein, in (A), lane M1: DNA ladder (100-3000 bp), and lane 1: GMNL-76; in (B), lane M2: DNA ladder (100-3000 bp), and lane 2: BCRC 12933; and in (C), lane M3: DNA ladder (100-3000 bp), and lane 3: BCRC 17500;

FIG. 6 shows a 16S rDNA nucleotide sequence SEQ ID NO: 5 of *Lactobacillus* GMNL-89.

DETAILED DESCRIPTION OF THE PREFERRED EMBODIMENTS

Figure 1:
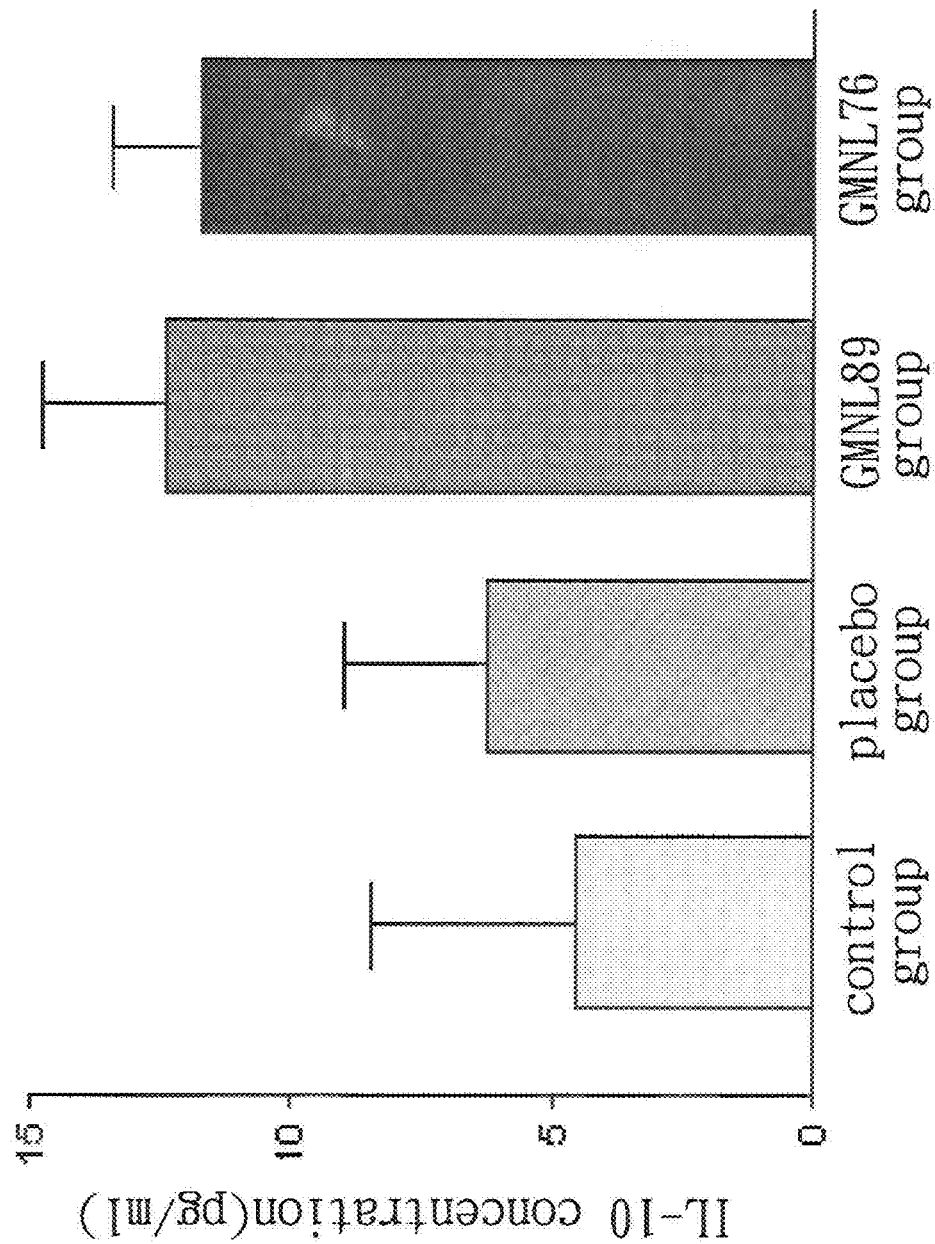
FIG. 1 shows ELISA test results for IL-10 in serum obtained from rats suffering from collagen-induced arthritis and fed with *Lactobacillus* GMNL-76 and GMNL-89 according to the present invention for eight consecutive weeks, in which rats free from arthritis and fed with RO water and rats with induced arthritis and fed with RO water serve as a control group and a placebo group, respectively.

Rheumatoid arthritis is a systemic chronic disease. However, clinically used drugs are unable to effectively treat rheumatoid arthritis. Moreover, long-term use of such medications may induce undesirable side effects.

In addition, prior studies have indicated that proinflammatory cytokines (such as IFN-γ and TNF-α) promote inflammation so that rheumatoid arthritis worsens. Immunoregulatory cytokines associated with Th2 cells (such as IL-10 and IL-4) can inhibit production of proinflammatory cytokines and can reduce cartilage destruction through inducing production of TIMPs. Therefore, it is hypothesized that the treatment of rheumatoid arthritis may be achieved by regulating secretion of immunoregulatory cytokines and proinflammatory cytokines.

Lactic acid bacteria, particularly bacterial strains of the genus *Lactobacillus*, are well known and widely used probiotic microbes. They have been proven to have many probiotic effects on the host, for example, improving the balance of normal intestinal microflora, preventing diarrhea, reducing the risk of colon cancer, stimulating normal development and functions of gastrointestinal epithelial cells, promoting the synthesis of vitamins and the production of enzymes, and preventing and treating vaginosis.

Therefore, the Applicants attempted to find *Lactobacillus* isolates with beneficial anti-inflammatory activity from lactic acid bacteria, which are considered as probiotic microorganisms, for treating rheumatoid arthritis.

Accordingly, gastrointestinal tract specimens obtained from healthy adult subjects of Taiwan were used as separated original sources of *Lactobacillus* isolates. The isolates were respectively co-cultured with monocytes of experimented animals so as to stimulate the monocytes to secret cytokines. Using IL-10 and IFN-γ as screening markers, two *Lactobacillus* isolates, i.e., GMNL-76 and GMNL-89, having the ability to stimulate the monocytes to secrete large amounts of IL-10 and a relatively small amount of IFN-γ and/or TNF-α were obtained. The two *Lactobacillus* isolates thus obtained were tested for purposes of characterization, and were identified and designated as *Lactobacillus sakei* and *Lactobacillus reuteri*, respectively.

*Lactobacillus sakei* GMNL-76 and *Lactobacillus reuteri* GMNL-89 were respectively deposited in the Biosource Collection and Research Center (BCRC) of the Food Industry Research and Development Institute (FIRDI) (331 Shih-Pin Road, Hsinchu city 300, Taiwan, R.O.C.) on Jun. 14, 2007, and Nov. 14, 2006, under accession numbers BCRC 910355 and BCRC 910340, respectively. These isolates were also deposited in the China Center for Type Culture Collection (CCTCC) (Wuhan University, Wuhan, 430072, People's Republic of China) under the Budapest Treaty on Nov. 19, 2007 under accession numbers CCTCC M 207153 and CCTCC M 207154, respectively.

When *Lactobacillus sakei* GMNL-76 and *Lactobacillus reuteri* GMNL-89 according to the present invention were fed to rats with collagen-induced arthritis, a rise of IL-10 and a reduction of IFN-γ and TNF-α in rat serum were observed. This indicates that *Lactobacillus sakei* GMNL-76 and *Lactobacillus reuteri* GMNL-89 according to the present invention have the ability to alleviate arthritis in rats.

Compared with known strains of *Lactobacillus sakei* BCRC 12933 and BCRC 17500, and known strains of *Lactobacillus reuteri* BCRC 14625, BCRC 16090, BCRC 16091, BCRC 17476, and BCRC 17478, the ability of *Lactobacillus sakei* GMNL-76 and *Lactobacillus reuteri* GMNL-89 to stimulate IL-10 secretion by monocytes in vitro is better than that of other known strains of the species to which they belong.

In view of the beneficial biological activities mentioned above, the two *Lactobacillus* isolates or their sub-cultured offspring are anticipated to have potential in the treatment of diseases associated with inflammation. Accordingly, the present invention provides a pharmaceutical composition for treating an inflammation-associated disease. The pharmaceutical composition comprises:

(i) at least one deposited strain selected from:
(a) *Lactobacillus sakei* GMNL-76 deposited in the Biosource Collection and Research Center (BCRC) of the Food Industry Research and Development Institute (FIRDI) under an accession number BCRC 910355 and deposited in the China Center for Type Culture Collection (CCTCC) under an accession number CCTCC M 207153; and
(b) *Lactobacillus reuteri* GMNL-89 deposited in the Biosource Collection and Research Center (BCRC) of the Food Industry Research and Development Institute (FIRDI) under an accession number BCRC 910340 and deposited in the China Center for Type Culture Collection (CCTCC) under an accession number CCTCC M 207154; or
(ii) a sub-cultured offspring of the deposited strain (i).

The present invention also provides a method for treating an inflammation-associated disease in a subject, comprising administering to a subject in need of the treatment one of the isolated *Lactobacillus* strain and a sub-cultured offspring thereof.

According to the present invention, the inflammation-associated disease is selected from rheumatoid arthritis, osteoarthritis, juvenile rheumatoid arthritis, ankylosing spondylitis, spondylitis, psoriatic arthritis, Crohn's disease, ulcerative colitis, and psoriasis. (Eveline Trachsel et al. (2007), *Arthritis Research & Therapy*, 9(1): R9, Published online Jan. 29, 2007. doi: 10.1186/ar2115; Suchita Nadkarni et al. (2007), *The Journal of Experimental Medicine*, 204:33-39; Richard O Williams et al. (2007), *Current Opinion in Pharmacology*, 7:412-417). In a preferred embodiment of this invention, the inflammation-associated disease is rheumatoid arthritis.

In the pharmaceutical composition according to this invention, the aforesaid *Lactobacillus* isolate or sub-cultured offspring thereof may be formulated with a pharmaceutically acceptable vehicle, and made into a dosage form suitable for oral administration using techniques known in the art of drug-making. In a preferred embodiment of this invention, the pharmaceutical composition is a dosage form selected from the group consisting of the following: solution, suspension, emulsion, powder, tablet, pill, syrup, lozenge, troche, chewing gum, capsule, slurry and the like.

As used herein, the term "pharmaceutically acceptable vehicle" refers to a vehicle that, when administered to a subject, will not result in an allergic reaction or other undesirable effects in the subject. According to the invention, the pharmaceutically acceptable vehicle includes one or more of the following: solvent, emulsifier, suspending agent, decomposer, binding agent, excipient, stabilizing agent, chelating agent, diluent, gelling agent, preservative, lubricant and the like.

In addition, the *Lactobacillus sakei* GMNL-76 and *Lactobacillus reuteri* GMNL-89 according to the present invention are also found to have resistance to bile salts and gastric acid, and are therefore suitable for use as gastrointestinal probiotics. For example, these two isolates and their sub-cultured offspring can be used as food additive components which, according to known methodologies, may be added during preparation of the food ingredients, or may be added after fermentation of the food ingredients if participation of the same in the fermentation process is not desired, so as to be formulated with any edible material into food products suitable for ingestion by humans or animals.

The present invention also provides a food product, which comprises the aforesaid *Lactobacillus* isolate or the offspring thereof and an edible material.

Edible materials suitable for the present invention include, but are not limited to: fluid milk products, e.g., milk and concentrated milk; fermented milk, e.g., yogurt, sour milk, frozen yogurt, and lactic acid bacteria-fermented beverages; milk powder; ice cream; cream cheeses; dry cheeses; soybean milk; fermented soybean milk; vegetable-fruit juices; fruit juices; sports drinks; confectionery; jelly; candies; infant formulas; health foods; animal feeds; dietary supplements, etc.

In addition, the food product according to the present invention may be in the form of instant food products that contain lyophilized or spray-dried isolated strain powders that can be directly consumed. For the preparation of relevant food products, reference can be made to, e.g., U.S. Pat. No. 6,872,565 B2, U.S. Pat. No. 7,244,424 B2, U.S. Pat. No. 7,270,994 B2, U.S. Pat. No. 7,172,777 B2, and U.S. Pat. No. 6,872,411 B1.

The food product according to the present invention may further comprise at least one probiotic microbes. As used herein, the terms "probiotic microbes" and "probiotics" are used interchangeably, and refer to preparations of live microorganisms. These microorganisms may remain and survive in the gastrointestinal tract after being ingested by a human or an animal, and can exert a preventive or therapeutic effect.

Probiotic microorganisms suitable for use in the present invention include, but are not limited to, *Lactobacillus* sp., *Bifidobacterium* sp., *Streptococcus* sp., yeasts, and their combinations.

Preferably, the *Lactobacillus* sp. is selected from the group consisting of the following: *Lactobacillus acidophilus*, *Lactobacillus lactis*, *Lactobacillus helveticus*, *Lactobacillus brevis*, *Lactobacillus casei*, *Lactobacillus plantarum*, *Lactobacillus salivarius*, *Lactobacillus bifidus*, *Lactobacillus bulgaricus*, *Lactobacillus caucasicus*, *Lactobacillus rhamnosus*, *Lactobacillus gasseri*, and their combinations.

Preferably, the *Bifidobacterium* sp. is selected from the group consisting of the following: *Bifidobacterium bifidum*, *Bifidobacterium longum*, *Bifidobacterium infantis*, *Bifidobacterium breve*, *Bifidobacterium adolescentis*, *Bifidobacterium lactis*, and their combinations.

Preferably, the *Streptococcus* sp. is selected from the group consisting of the following: *Streptococcus thermophilus*, *Streptococcus lactis*, *Streptococcus cremoris*, *Streptococcus diacetylcatis*, and their combinations.

Preferably, the yeast is selected from the group consisting of the following: *Candida Kefyr, Saccharomyces florentinus, Saccharomyces cereviseae*, and their combinations.

EXAMPLES

Example 1

Preliminary Screening of *Lactobacillus* Isolates having Anti-Inflammatory Activity Materials and Methods
A. Source and Preparation of Tested Strains Applicants obtained specimens from gastrointestinal tracts of a number of healthy adults at the China Medicine University Hospital (Taichung, Taiwan) in January 2002. About 400 isolated strains of *Lactobacillus* were screened from the specimens. In order to search for probiotics that have potential in treating rheumatoid arthritis, Applicants analyzed the isolated strains for anti-inflammatory activities, using IL-10 as a screening marker.

A Bacto Lactobacilli MRS broth medium (DIFCO, Cat. No. 0881) was inoculated with a tested strain, followed by anaerobic culture at 37° C. for 12 to 18 hours. The resultant bacterial culture was centrifuged at 4,000 rpm for 15 minutes. After removal of the supernatant, the precipitate was washed thrice in 1× phosphate buffered saline (PBS), followed by suspension in 1×PBS. The concentration of the resultant bacterial solution was adjusted to 1~5×10$^9$ cells/mL (the number of bacteria was counted using $OD_{600}$, $OD_{600}$=1.00=5.0×10$^8$ cells/mL) using 1×PBS, and the bacterial solution thus adjusted was used as a stock solution for 10-fold serial dilution to obtain testing solutions of 10$^8$, 10$^7$, 10$^6$, 10$^5$, 10$^4$, 10$^3$, 10$^2$, 10$^1$ cells/mL.

B. Preparation of Mouse Spleen Monocytes:

Female BALB/c mice of 6-8 weeks old were sacrificed using CO2, and the spleens were taken out and were ground using a sterilized glass rod. The spleen tissues obtained after grinding were subjected to density gradient centrifugation (720 g×20 min, below 4° C.) with Ficoll-Paque™ PLUS (17-1441-03, Amersham Biosciences) at a volume ratio of 1:1. Thereafter, red blood cells were removed to thereby obtain mouse spleen monocytes, and the concentration of the cells were adjusted to 4×10$^6$ cells/mL using an RPMI 1640 medium containing 10% fetal bovine serum (FBS).

C. Evaluation of IL-10 Secretion by Mouse Spleen Monocytes Stimulated by *Lactobacillus* Isolates:

To each well of a 96-well culture plate was added 100 µL of 4×10$^6$ cells/mL samples of the spleen monocytes prepared in Item B. The samples were divided into an experimental group, a normal control group, and a positive control group. In the experimental group, each well was further added with 20 µL of the testing bacterial solution prepared in Item A. In the normal control group, each well was further added with 20 µL RPMI 1640 medium containing 10% FBS. In the positive control group, each well was further added with 20 µL of lipopolysaccharides (LPS) (*Escherichia coli*, serotype O55: B5, Sigma). After incubation in an incubator (37° C., 5% CO2) for a period of 24 hours, the culture solution in each well was drawn out and centrifuged. 100 µL of the supernatant was taken out for conducting an enzyme linked immunosorbent assay (ELISA) using Mouse IL-10 OptEIA™ Set (BD Biosciences, Cat. No. 555252). The experiment was repeated twice for each group.

The concentration of IL-10 was calculated by substituting the $OD_{405}$ values obtained with ELISA into the following equation, and was expressed in ELISA unit (%)

ELISA unit(%)=[(A−C)/(B−C)]×100 where:

A=$OD_{405}$ value of *Lactobacillus* isolates;

B=$OD_{405}$ value of the positive control group; and

C=$OD_{405}$ value of the normal control group.

Result:

Of all the experimented strains, 46 strains stimulated higher IL-10 secretion by mouse spleen monocytes. The experimental results are shown in Table 1.

TABLE 1

| Tested strain number | ELISA unit (%) | |
|---|---|---|
| | Experiment 1 | Experiment 2 |
| GMNL-11 | 74.4616 | 69.7510 |
| GMNL-18 | 95.3230 | 104.7443 |
| GMNL-19 | 75.8075 | 64.3674 |
| GMNL-22 | 71.0969 | 112.1467 |
| GMNL-27 | 155.2153 | 157.2342 |
| GMNL-28 | 266.2517 | 277.0188 |
| GMNL-32 | 147.8129 | 152.5236 |
| GMNL-33 | 151.1777 | 143.1023 |
| GMNL-34 | 30.7201 | 34.757740 |
| GMNL-35 | 61.6756 | 34.0848 |
| GMNL-36 | 34.0848 | 36.7766 |
| GMNL-37 | 45.5249 | 39.4683 |
| GMNL-38 | 36.1036 | 33.4118 |
| GMNL-39 | 44.8520 | 44.1790 |
| GMNL-41 | 87.9206 | 95.3230 |
| GMNL-42 | 98.6878 | 95.3230 |
| GMNL-43 | 157.9071 | 151.8506 |
| GMNL-44 | 69.75101 | 54.9462 |
| GMNL-45 | 273.6541 | 186.8439 |
| GMNL-47 | 31.3930 | 28.7012 |
| GMNL-50 | 223.1830 | 168.001 |
| GMNL-55 | 174.7308 | 161.9448 |
| GMNL-57-I | 148.4859 | 153.8694 |
| GMNL-57-II | 230.5855 | 268.2705 |
| GMNL-67 | 242.6985 | 215.7806 |
| GMNL-68 | 114.1655 | 91.9583 |
| GMNL-69 | 128.9704 | 113.4926 |
| GMNL-76 | 167.3284 | 146.4670 |
| GMNL-78 | 198.9569 | 221.1642 |
| GMNL-84 | 73.7887 | 75.1346 |
| GMNL-87 | 32.7389 | 34.7577 |
| GMNL-88 | 40.8143 | 46.8708 |
| GMNL-89 | 54.2732 | 54.2732 |
| GMNL-94 | 237.3149 | 225.2019 |
| GMNL-97 | 166.6555 | 176.7497 |
| GMNL-101 | 355.7537 | 395.4576 |
| GMNL-126 | 151.1777 | 141.7564 |
| GMNL-127 | 196.9381 | 178.7685 |
| GMNL-128 | 682.1332 | 450.6393 |
| GMNL-130 | 498.4186 | 293.8425 |
| GMNL-131 | 341.6218 | 480.9219 |
| GMNL-132 | 435.1615 | 361.8102 |
| GMNL-133 | 302.5909 | 268.9435 |
| GMNL-138 | 672.0390 | 446.6016 |
| GMNL-139 | 400.8412 | 403.5330 |
| GMNL-161 | 304.6097 | 339.6030 |

According to the experimental results in Table 1, and taking into consideration factors such as growth rate of the tested strains, number of bacteria, utility in terms of mass production, etc., the Applicants selected GMNL-19, GMNL-76, GMNL-78, GMNL-89, GMNL-94, GMNL-101, and GMNL-161 for further experimentation to evaluate the abilities of these strains to stimulate secretion of IL-10 and IFN-γ by human peripheral blood mononuclear cells (human PBMCs).

Example 2

Evaluation of the Ability of *Lactobacillus* Isolates to Stimulate Secretion of IL-10 and IFN-γ by Human PBMCs Materials and Methods:

A. Preparation of Human PBMCs:

Human white blood cell concentrate (Tainan blood donation center) that has been inspected to be suitable for experimentation purposes were subjected to density gradient centrifugation (720 g, 20 min) at 4° C. with Ficoll-Paque™ PLUS (17-1441-03, Amersham Biosciences) at a volume ratio of 1:1. Thereafter, the red blood cells were removed to thereby obtain human PBMCs, and the cell concentration was adjusted to $4 \times 10^6$ cells/mL using an RPMI 1640 medium containing 10% FBS.

B. Evaluation of IL-10 Secretion by Human PBMCs Stimulated by *Lactobacillus* Isolates:

The evaluation of the ability of *Lactobacillus* isolates GMNL-19, GMNL-76, GMNL-78, GMNL-89, GMNL-94, GMNL-101, and GMNL-161 to stimulate secretion of IL-10 by human PBMCs is essentially based on the operating procedure described in connection with Item C of Example 1. The difference resides in that a 20 μL testing bacterial solution having a concentration of $1 \times 10^8$ cells/mL was used as the experimental group, and 100 μL of samples of the human PBMCs prepared in Item A, and Human IL-10 OptEIA™ Set (BD Biosciences, Cat. No. 555157) were used.

C. Evaluation of Secretion of IFN-γ by PBMCs Stimulated by *Lactobacillus* Isolates:

The ability of *Lactobacillus* isolates GMNL-19, GMNL-76, GMNL-78, GMNL-89, GMNL-94, GMNL-101, and GMNL-161 to stimulate secretion of IFN-γ by human PMBCs was analyzed in accordance with the following description.

To each well of a 96-well culture plate was added 100 μL of the samples of human PBMCs. The samples were divided into an experimental group and a normal control group. In the experimental group, 20 μL of the testing bacterial solution ($1 \times 10^7$ cells/mL) prepared in Item A of Example 1 was further added to each well. In the normal control group, 20μ of RPMI 1640 medium containing 10% FBS was further added to each well. After incubation in an incubator (37° C., 5% CO2) for a period of 24 hours, the culture solution in each well was centrifuged. 100 μL of the supernatant removed therefrom was taken out for conducting IFN-γ ELISA using BD OptEIA™ Human IFN-γ ELISA Kit II (BD Biosciences, Cat. No. 550612).

In addition, samples of human PBMCs were added with *Phaseolus vulgaris* agglutinin (PHA, Sigma, Cat. No. L2769) at a ratio of $4 \times 10^6$ cells/mL to 10 μg/mL of PHA, and were cultured for a period of 48 hours. After centrifugation (720 g×20 min, 4° C.), the supernatant was taken out and stored in a freezer set to −80° C. The PHA-processed supernatant (100 mL) was used as an internal positive control when conducting an analysis of IFN-μ ELISA.

100 μL of mouse anti-human IFN-γ (BD Pharmingen™, Cat. No. 551221) diluted 1000-fold by a coating buffer (0.1 M Na2HPO4, 0.77 mM NaN3, pH 9.0) was added to each well of a 96-well culture plate (Nunc-Immuno™ 96 MicroWell™ Plates, MaxiSorp, Cat. No. 442404). The culture plate was agitated at 40 rpm at room temperature (25° C.) for 1 hour, followed by cultivation at 4° C. overnight.

Thereafter, the culture plate was restored to room temperature, and the liquid in each well was removed. Each well was washed twice (3 min each) using a washing buffer (PBS containing 0.05% Tween 20), followed by addition of 200 mL of a blocking buffer (PBS containing 3% Bovine Serum Albumin) to each well. The culture plate was allowed to stand at room temperature for 2 hours, followed by removal of the blocking buffer and washing with the washing buffer twice.

100 μL of the sample to be tested was added to each well, and was allowed to react at 4° C. overnight. Thereafter, the liquid in each well was removed, and each cell was washed twice with a washing buffer (PBS containing 0.05% Tween 20). Subsequently, 100 mL of biotin mouse anti-human IFN-γ (BD Pharmingen™, Cat. No. 554550) diluted 2000 times with a diluent buffer (PBS containing 1% BSA) was added to each well, and was allowed to react at room temperature for 2 hours. After the liquid in each well was removed, each well was washed twice with a washing buffer (PBS containing 0.05% Tween 20). Thereafter, 100 mL of Streptavidin-Alkaline phophatase (Streptavidin-AP, BD Pharmingen™, Cat. No. 554065) diluted 2000 times with a diluent buffer (PBS containing 1% BSA) was allowed to react at room temperature for 1 hour. After the liquid in each well was removed, each cell was washed four times with a washing buffer (PBS containing 0.05% Tween 20), followed by addition of 100 mL freshly prepared p-Nitrophenylphosphate (pNPP) solution to each well. The culture plate was placed in a dark place at room temperature and allowed to react for 30 minutes. Thereafter, the absorbance at 405 nm was read for each well using ELISA Microplate Reader (Bio-Rad, Model 550). This experiment was repeated twice for each group.

The concentration of IFN-γ was calculated by substituting the $OD_{405}$ values obtained with ELISA into the following equation, and was expressed in ELISA unit (%):

$$\text{ELISA unit}(\%) = [(A-C)/(B-C)] \times 100$$

where:
$A = OD_{405}$ value of *Lactobacillus* isolates;
$B = OD_{405}$ value of the internal positive control group; and
$C = OD_{405}$ value of normal control group.

Result:

The results of IL-10 and INF-γ secretion by human PBMCs stimulated by *Lactobacillus* isolates GMNL-19, GMNL-76, GMNL-78, GMNL-89, GMNL-94, GMNL-101, and GMNL-161 are respectively shown in Tables 2 and 3.

TABLE 2

| *Lactobacillus* | ELISA unit (%) | |
|---|---|---|
| isolate number | Experiment 1 | Experiment 2 |
| GMNL-19 | 26.5578 | 27.5374 |
| GMNL-76 | 56.3810 | 57.7959 |
| GMNL-78 | 50.1769 | 56.0544 |
| GMNL-89 | 104.3810 | 118.3129 |
| GMNL-94 | 45.1701 | 47.5646 |
| GMNL-101 | 54.7483 | 54.3129 |
| GMNL-161 | 44.4082 | 52.5714 |

TABLE 3

| *Lactobacillus* | ELISA unit (%) | |
|---|---|---|
| isolate number | Experiment 1 | Experiment 2 |
| GMNL-19 | 137.2893 | 124.8361 |
| GMNL-76 | 92.9073 | 103.6751 |
| GMNL-78 | 36.1657 | 35.3230 |
| GMNL-89 | 64.6302 | 59.9485 |
| GMNL-94 | 105.2669 | 89.9111 |
| GMNL-101 | 152.9260 | 157.6077 |
| GMNL-161 | 205.0796 | 215.0047 |

It can be seen from Table 2 that, of all the *Lactobacillus* isolates, GMNL-76 and GMNL-89 stimulated the highest amount of secretion of IL-10 by human PBMCs. This indicates that the ability of these *Lactobacillus* isolates to stimulate secretion of IL-10 by human PBMCs is the highest.

It is further apparent from Table 3 that, of all the *Lactobacillus* isolates, GMNL-78 stimulated the least amount of secretion of IFN-γ by human PBMCs, with GMNL-89 and GMNL-76 second thereto. This indicates that the ability of GMNL-78 to stimulate secretion of IFN-γ by human PBMCs is the lowest, and the abilities of GMNL-89 and GMNL-76 are likewise quite low.

Proinflammatory cytokines (such as IFN-γ and TNF-α) are known to promote inflammation to result in aggravated rheumatoid arthritis, whereas immunoregulatory cytokines (such as IL-10) are known to be able to inhibit formation of proinflammatory cytokines. The Applicants therefore hypothesize that: if human or animal monocytes could be stimulated to secrete more immunoregulatory cytokines and less proinflammatory cytokines, rheumatoid arthritis conditions in human or animals could be improved. Furthermore, according to the results in Tables 2 and 3, the Applicants believe that *Lactobacillus* isolates GMNL-76 and GMNL-89 showed more potential for development, and were used in the animal tests described below.

Example 3

Evaluation of the Therapeutic Effect of *Lactobacillus* Isolates GMNL-76 and GMNL-89 on Rats with Collagen-Induced Arthritis Materials and Methods:
A. Animals:

Male LEW/SsNNarl rats (6-week old, weighing about 200 to 250 g) purchased from the Laboratory Animal Center, National Applied Research Laboratories (Taiwan) were used in the following experiments. All the animals were housed in a separate air-conditioned room maintained at a temperature of 25±1° C. and a relative humidity of 60±5%, and were given 12-hour lighting. The animals were allowed access to sufficient water and food, and were acclimatized to the test environment for a week. Animal handling and the experiment protocol conformed to the standards of the Laboratory Animal Committee, Taiwan.

B. Preparation of Test Strains:

Bacto Lactobacilli MRS broth media (DIFCO, Cat. No. 0881) were respectively inoculated with *Lactobacillus* isolates GMNL-76 and GMNL-89. The isolates were cultured anaerobically at 37° C. until growth was saturated. After centrifugation at 3,000 g for 15 minutes, the precipitate was washed twice with 2 mL and 1 mL of 1×PBS (pH 7.2), respectively, followed by addition of 1 mL of PBS thereto. The concentration of the bacterial solutions was measured using $OD_{600}$. The measured concentration was approximately $1.0 \times 10^{10}$ cells/mL. The bacterial solution was stored at −80° C. for subsequent use.

C. Induction of Arthritis:

The induction of arthritis was conducted using a method that was slightly modified from that described by Y. Kameyama et al. in *Bone* 35 (2004) 948-956. Bovine type II collagen (CII for short) (Sigma-Aldrich, Cat. No. C1188) was dissolved in 0.05 M acetic acid to formulate a CII solution having a concentration of 2 mg/mL. A CII emulsion was formulated from 100 μL of CII solution and 100 μL complete Freund's adjuvant (CFA). Thereafter, 200 μL of the CII emulsion was injected subcutaneously into the tails of the rats. The rats were given a boost injection twenty-one days after the initial immunization.

D. Feeding with *Lactobacillus* Isolates:

The rats were randomly divided into four groups (n=6 per each group), including three experimental groups (GMNL-76 group, GMNL-89 group, and placebo group) and a control group. Except for the control group, arthritis induction was performed on the rats in all the other groups according to the method described in Item C of this example.

For the GMNL-76 group and the GMNL-89 group, starting from the seventh day after the boost injection, the rats were fed with the bacterial solution ($1.0 \times 10^{10}$ cells/mL/day) prepared in Item B of this example. The rats in the placebo group and the control group were fed with reverse-osmosis (RO) water.

After feeding for eight consecutive weeks, blood of the rats was collected by orbital bleeding for centrifugation. The resulting serum was used for measuring concentrations of IL-10, IFN-γ and TNF-α. In addition, all the rats were further used for the following evaluation of arthritis after orbital bleeding.

E. Measurement of Concentrations of IL-10, IFN-γ and TNF-α:

Evaluation of IL-10 concentration was essentially based on the operating procedure described in Item C of Example 1, except that the rat serum obtained in Item D of this example and a Rat IL-10 OptEIA™ Set (BD Bioscience PharMingen, San Diego, Calif., Cat. No. 2611KI) were used.

Evaluation of IFN-γ concentration was essentially based on the operating procedure described in Item C of Example 2, except that the rat serum obtained in Item D of this example and a Rat IFN-γ OptEIA™ Set (BD Bioscience PharMingen, San Diego, Calif.) were used.

Evaluation of TNF-α concentration was essentially based on the operating procedure described in Item C of Example 1, except that the rat serum obtained in Item D of this example and a BD OptEIA Rat TNF-α ELISA Kit (BD Bioscience PharMingen, San Diego, Calif.) were used.

The $OD_{405}$ values thus obtained were subsequently converted to concentrations expressed in pg/mL based on a correlation curve previously prepared by plotting different known concentrations of IL-10, IFN-γ or TNF-α standards versus their $OD_{405}$ values.

F. Evaluation of Arthritis:

The evaluation of arthritis in the rats were based on the method described by Y. Kameyama et al. in *Bone* 35 (2004) 948-956. Specifically, changes, such as swelling and enlargement, in the joints of the four paws of each rat were recorded and quantified by scoring each paw on a scale from 0-4: 0, absence of arthritis symptoms; 1, swelling in one toe; 2, swelling in more than three toes; 3, swelling in the entire paw; 4, severe swelling and curling of all the joints, which prevent normal walking.

G. Statistical Analysis:

Statistical analysis was conducted using SPSS statistics software (version 10.0). Since the total number of the tested animals was less than thirty, the experimental data was analyzed using a nonparametric statistical method (also known as Mann-Whitney U test) for evaluating differences between the control group, the GMNL-76 group, the GMNL-89 group, and the placebo group in terms of sample distribution. The experimental data was expressed in mean±standard deviation (statistical significance, $P<0.05$)

Figure 2:
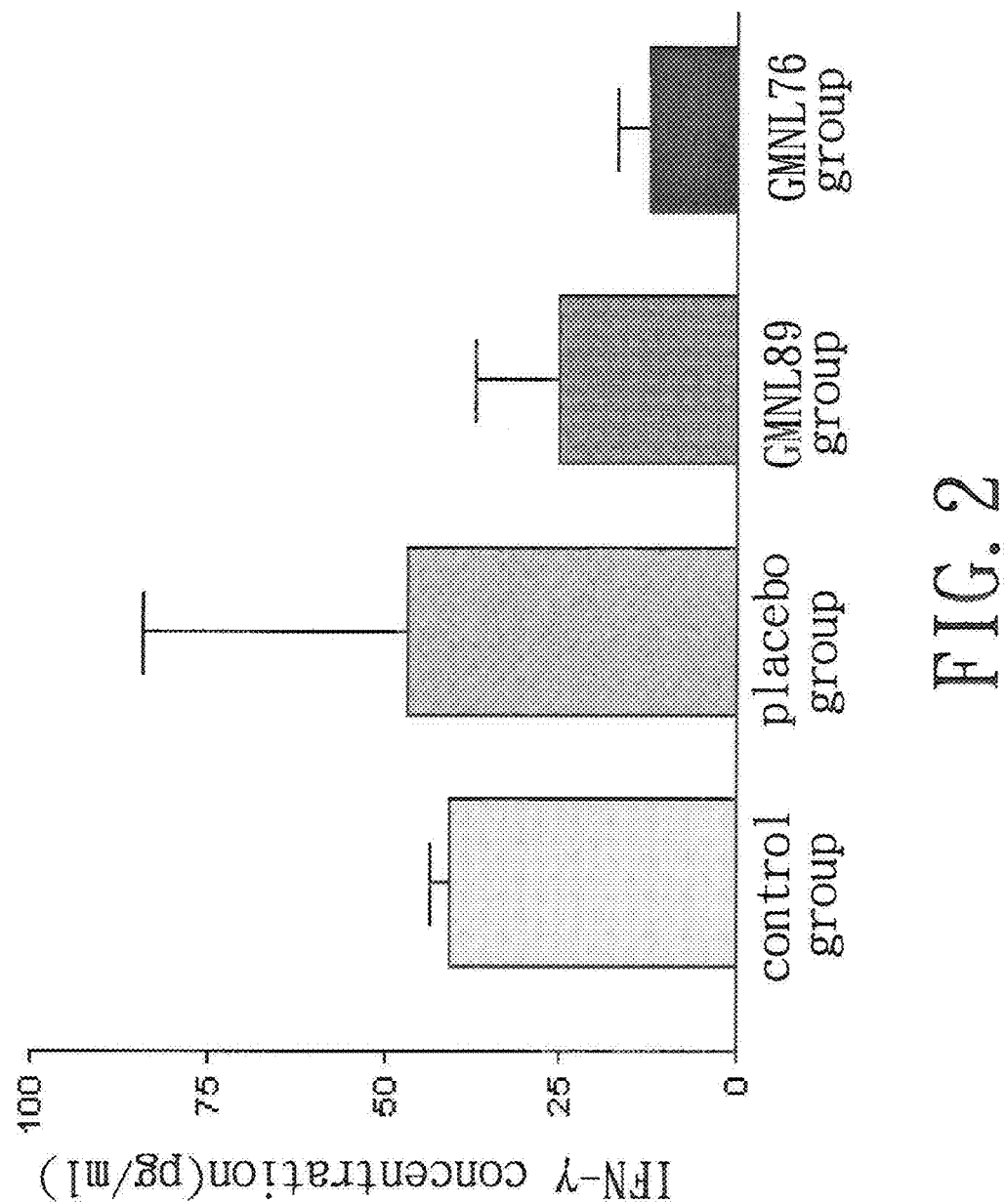
FIG. 2 shows ELISA test results for IFN-γ in serum obtained from rats suffering from collagen-induced arthritis and fed with *Lactobacillus* GMNL-76 and GMNL-89 according to the present invention for eight consecutive weeks, in which rats free from arthritis and fed with RO water and rats with induced arthritis and fed with RO water serve as a control group and a placebo group, respectively.
Figure 3:
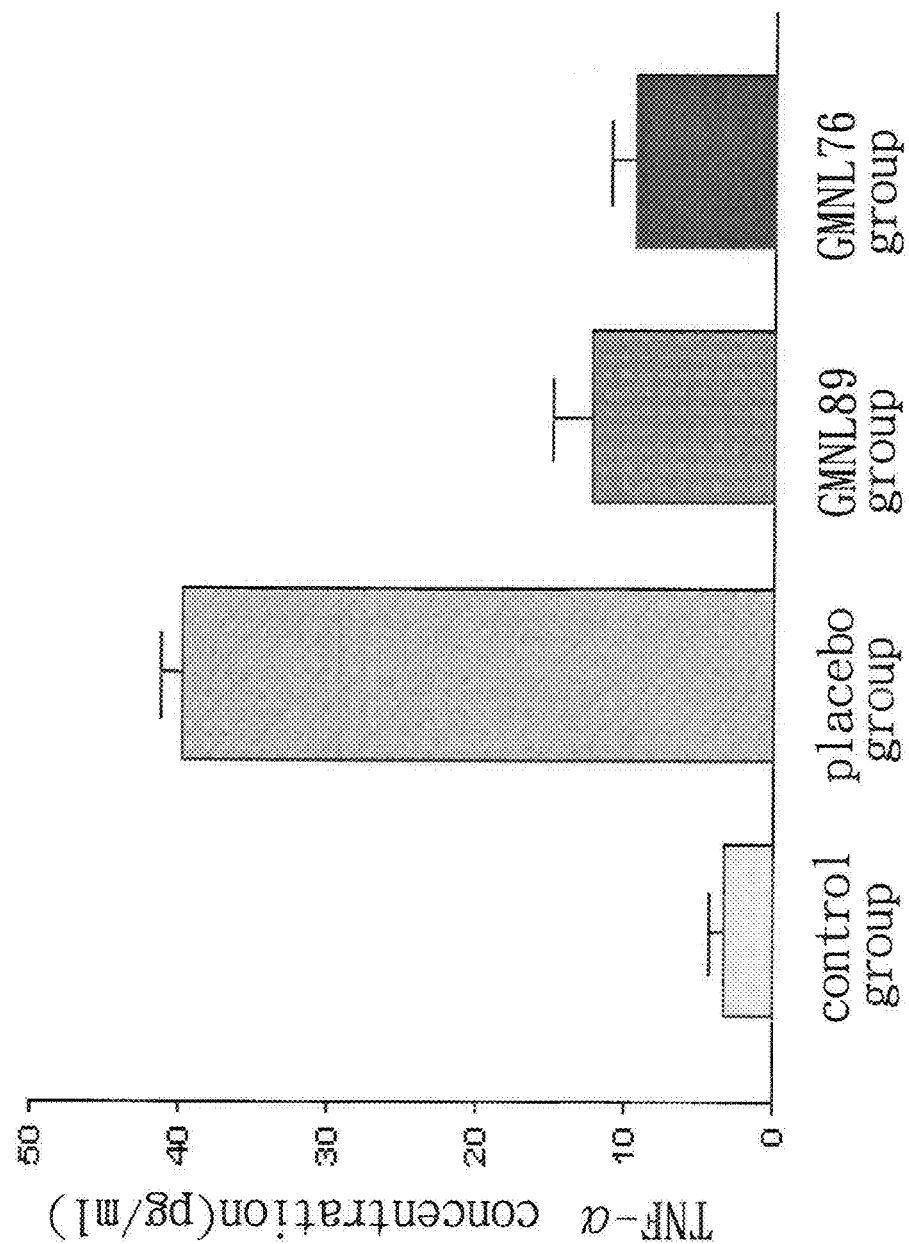
FIG. 3 shows ELISA test results for TNF-α in serum obtained from rats suffering from collagen-induced arthritis and fed with *Lactobacillus* GMNL-76 and GMNL-89 according to the present invention for eight consecutive weeks, in which rats free from arthritis and fed with RO water and rats with induced arthritis and fed with RO water serve as a control group and a placebo group, respectively.

Result:

The concentrations of IL-10, IFN-γ and TNF-α in the serum of rats fed for eight consecutive weeks are respectively shown in Table 4 and in FIGS. 1 to 3. In addition, the score results of the evaluation of arthritis are summed up in Table 4.

TABLE 4

| Items analyzed | Control group | Placebo group | GMNL-76 | GMNL-89 |
|---|---|---|---|---|
| IL-10 (pg/mL) | 4.56 ± 5.50 | 6.22 ± 4.811 | 11.78 ± 3.747 | 12.44 ± 5.232 |
| IFN-γ (pg/mL) | 40.60 ± 4.243 | 46.78 ± 52.64 | 12.20 ± 10.923 | 25.00 ± 26.482 |

TABLE 4-continued

| Items analyzed | Control group | Placebo group | GMNL-76 | GMNL-89 |
| --- | --- | --- | --- | --- |
| TNF-α (pg/mL) | 3.32 ± 1.757* | 39.80 ± 1.998 | 9.44 ± 3.988* | 12.20 ± 6.643* |
| Scores of severity of arthritis | 0* | 12.333 ± 1.155 | 11.67 ± 2.563 | 13.42 ± 2.155 |

1: All the data was analyzed using the Mann-Whitney U test.
2: The scores of severity of arthritis for each rat were calculated by summing the total scores for the joints in the four paws.
3: *: $p<0.05$, compared with placebo group.

It is apparent from Table 4 and FIGS. 1 to 3 that, for the rats in the GMNL-76 group and the GMNL-89 group, which were respectively fed with *Lactobacillus* isolates GMNL-76 and GMNL-89, the concentrations of IFN-γ and TNF-α in their serum were significantly lowered compared with the placebo group, whereas the concentrations of IL-10 were significantly increased.

Therefore, the Applicants hypothesize that: *Lactobacillus* isolates GMNL-76 and GMNL-89 can lower TNF-α secretion aside from lowering secretion of IFN-γ by Th1 cells to alleviate inflammation, thereby reducing secretion of MMPs to prevent further damage to cartilage in joint tissues. In addition, *Lactobacillus* isolates GMNL-76 and GMNL-89 can also increase the secretion of immunoregulatory cytokine, IL-10, to render the condition of inflammation controllable. Therefore, although joint damage caused by arthritis is irrevocable, through feeding with *Lactobacillus* isolates GMNL-76 and GMNL-89 of this invention, there is a reduction in inflammation-associated IFN-γ and TNF-α in the rat serum, while there is an increase in anti-inflammation-associated IL-10. This indicates that the arthritis condition in the rats was alleviated and did not aggravate.

Example 4

Identification and Characterization of *Lactobacillus* Isolates GMNL-76 and GMNL-89

In order to identify the species of the *Lactobacillus* isolates GMNL-76 and GMNL-89 screened in the above examples, the following preliminary tests, 16S rDNA sequence analysis, and Random Amplified Polymorphic DNA (RAPD) analysis were conducted.
Materials and Methods:
A. Preliminary Tests:
Items of the preliminary tests conducted against the *Lactobacillus* isolates GMNL-76 and GMNL-89 include: gram staining, morphological observation, catalase test, mobility, growth under aerobic and anaerobic conditions.
B. 16S rDNA Sequence Analysis:
Under sterile conditions, each of the isolates GMNL-76 and GMNL-89 was inoculated into 1 mL of Bacto Lactobacilli MRS broth medium (DIFCO, Cat. No. 0881), and cultured at 37° C. overnight. Thereafter, each of the bacterial solutions was centrifuged at 13,000 rpm for 1 minute, followed by removal of the supernatant. Each of the remaining precipitates was then suspended in 200 μL of ddH$_2$O, followed by centrifugation at 13,000 rpm for 1 minute and removal of the supernatant. This step was repeated once. Finally, each of the cell precipitates thus obtained by centrifugation was suspended in 200 μL of ddH$_2$O.

The cell suspension containing the genomic DNA was subjected to a polymerase chain reaction (PCR) performed under the reaction conditions shown in Table 5 using a primer pair (PAF primer and 536R primer) having the following nucleotide sequence and designed for a 16S rDNA sequence of *Lactobacillus* reported in an article by P. S. M. Yeung et al. (2002) (*J. Dairy Sci.*, 85:1039-1051).
PAF primer
5'-agagtttgatcctggctcag-3' (SEQ ID NO: 1)
536R primer
5'-gtattaccgcggctgctg-3' (SEQ ID NO: 2)

TABLE 5

| Content | Volume (μL) |
| --- | --- |
| Genomic DNA of *Lactobacillus* isolate | 0.5 |
| PAF primer (10 μM) | 1 |
| 536R primer (10 μM) | 1 |
| dNTPs (2.5 mM) | 1 |
| 10X Ex Taq buffer (TaKaRa) | 5 |
| TaKaRa Ex Taq ™ (TaKaRa) (5 U/μL) | 0.2 |
| Water | 41.3 |

Operating conditions: Denaturation was conducted at 94° C. for 30 seconds; primer annealing was conducted at 51° C. for 30 seconds; and elongation was conducted at 72° C. for 30 seconds; a total of thirty cycles were conducted.

After completion of the PCR, the resultant PCR products were subjected to electrophoresis on 1.8% agarose gels to verify whether a PCR amplified product of about 500 bp was obtained, and the verified PCR product was recovered and purified from the agarose gels. Sequences for the purified PCR product were determined by Genomics BioSci & Tech. Co., Ltd., Taiwan, and the determined sequences were compared and analyzed using the software nucleotide-nucleotide BLAST on NCBI website.
C. Random Amplified Polymorphic DNA (RAPD) Analysis:

After analyzing and verifying the species of *Lactobacillus* isolates GMNL-76 and GMNL-89 using the 16S rDNA sequences, the genomic DNAs of *Lactobacillus* isolates GMNL-76 and GMNL-89 obtained in Item B of this example were used as templates, and a 10-mer primer Lac P2 having the following nucleotide sequence and reported by M. de Angelis et al. (2001) in *Applied and Environmental Microbiology*, 67:2011-2020 was chosen for conducting PCR under the reaction conditions shown in Table 6.
Lac P2 primer
5'-atgtaacgcc-3' (SEQ ID NO: 3)

TABLE 6

| Content | Volume (μL) |
| --- | --- |
| Genomic DNA of *Lactobacillus* isolates | 1 |
| Lac P2 primer (10 μM) | 0.5 |
| dNTPs (2.5 mM) | 0.5 |
| 10X Ex Taq buffer (TaKaRa) | 2.5 |
| TaKaRa Ex Taq ™ (TakaRa) (5 U/μL) | 0.2 |
| Water | 20.3 |

Operating conditions: Denaturation was conducted at 93° C. for 1 minute; primer annealing was conducted at 36° C. for 1 minute; and elongation was conducted at 74° C. for 1 minute; a total of thirty cycles were conducted.

After completion of PCR, the amplified products were subjected to electrophoresis on 1.8% agarose gels, followed by staining, observation under ultraviolet light, and picture-taking.

Figure 7:
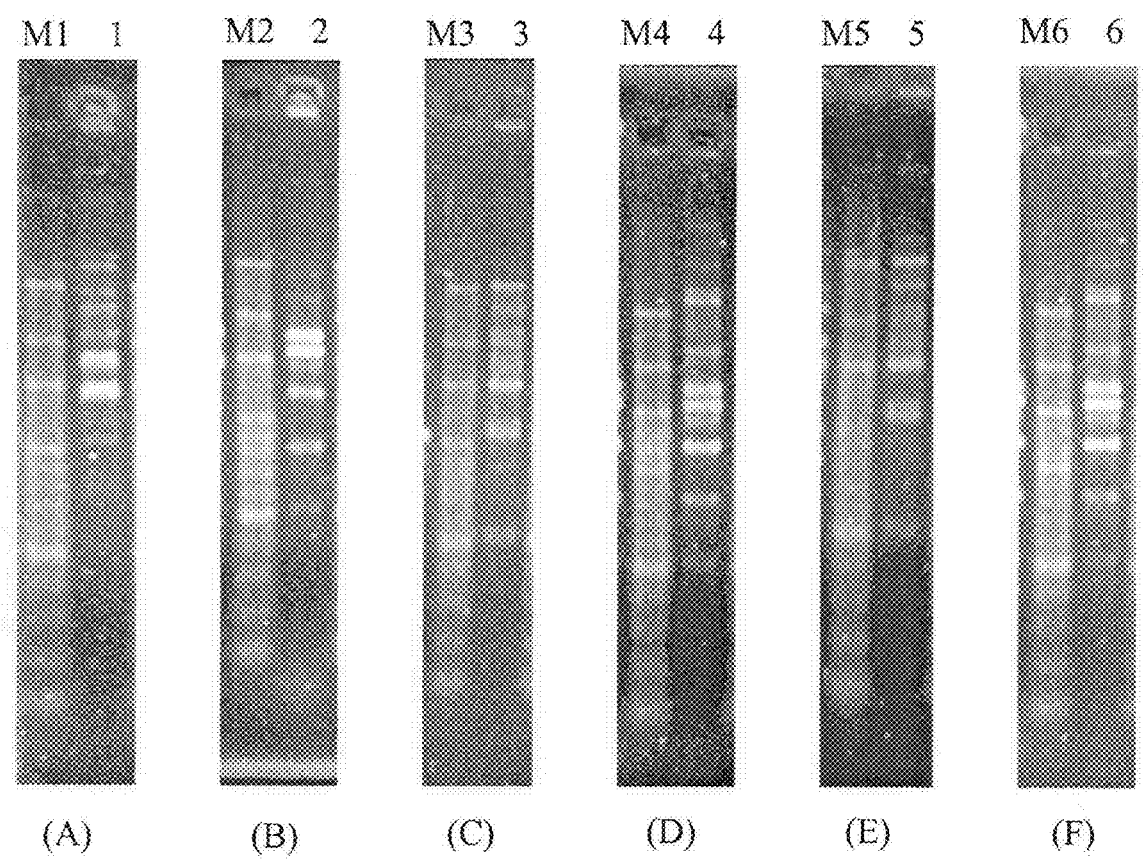
FIG. 7 shows photographic image results of electrophoresis on 1.8% agarose gel which was performed subsequent to a Random Amplified Polymorphic DNA (RAPD) analysis conducted using genomic DNAs of *Lactobacillus* GMNL-89 according to this invention and of five known strains of *Lactobacillus reuteri*, BCRC 14625, BCRC 16090, BCRC 16091, BCRC 17476 and BCRC 17478, as templates and using Lac P2 primer(s), wherein, in (A), lane M1: DNA ladder (100-3000 bp), and lane 1: GMNL-89; in (B), lane M2: DNA ladder (100-3000 bp), and lane 2: BCRC 14625; in (C), lane M3: DNA ladder (100-3000 bp), and lane 3: BCRC 16090; in (D), lane M4: DNA ladder (100-3000 bp), and lane 4: BCRC 16091; in (E), lane M5: DNA ladder (100-3000 bp), and lane 5: BCRC 17476; and in (F), lane M6: DNA ladder (100-3000 bp), and lane 6: BCRC 17478.

In this experiment, seven strains of *Lactobacillus* strains were also purchased from the BCRC of the FIRDI, Taiwan, to serve as controls for purposes of comparison and analysis. The seven strains include:
1. *Lactobacillus sakei* subsp. *sakei*, BCRC 12933 (corresponding to ATCC 31063; isolated from pickled cabbage);
2. *Lactobacillus sakei* subsp. *carnosus*, BCRC 17500 (corresponding to LMG 17302; isolated from raw sausage);
3. *Lactobacillus reuteri*, BCRC 14625 (corresponding to ATCC 23272 and DSM 20016; isolated from human feces);
4. *Lactobacillus reuteri*, BCRC 16090 (corresponding to DSM 20015; isolated from manure);
5. *Lactobacillus reuteri*, BCRC 16091 (corresponding to DSM 20053; isolated from human feces);
6. *Lactobacillus reuteri*, BCRC 17476 (corresponding to JCM 1081; isolated from chicken intestine); and
7. *Lactobacillus reuteri*, BCRC 17478 (corresponding to JCM 2762; isolated from fermented molasses).
Result:
1. Identification and Characterization of *Lactobacillus* Isolate GMNL-76:
    (i) According to the preliminary test results, this isolate is gram-positive, non-motile, catalase-negative, and oxidase-negative, and grows under both aerobic and anaerobic conditions.
    (ii) The analysis results of the 16S rDNA sequence of this isolate are shown in FIG. 4. After a comparison with the gene database on NCBI's website, it is found that the 16S rDNA sequence (SEQ ID NO: 4) of this isolate is most homologous to that of *Lactobacillus sakei*; and
    (iii) The RAPD analysis results are shown in FIG. 5. As shown, the gene fingerprint profile of the PCR product of this isolate is different from those of the other two known strains of *Lactobacillus sakei*, BCRC 12933 and BCRC 17500.
In view of the above identification results, the *Lactobacillus* isolate GMNL-76 according to this invention is believed to be a new isolate of *Lactobacillus sakei*.
2. Identification and Characterization of *Lactobacillus* Isolate GMNL-89:
    (i) According to the preliminary test results, this isolate is gram-positive, non-motile, catalase-negative, and oxidase-negative, and grows in both aerobic and anaerobic conditions;
    (ii) The analysis results of the 16S rDNA sequence of this isolate are shown in FIG. 6. After a comparison with the gene database on NCBI's website, it is found that the 16S rDNA sequence (SEQ ID NO: 5) of this isolate is most homologous to that of *Lactobacillus reuteri*; and
    (iii) The RAPD analysis results are shown in FIG. 7. As shown, the gene fingerprint profile of the PCR product of this isolate is different from those of the other five known strains of *Lactobacillus reuteri*, BCRC 14625, BCRC 16090, BCRC 16091, BCRC 17476, and BCRC 17478.
In view of the above identification results, it is believed that the *Lactobacillus* isolate GMNL-89 according to this invention is a novel isolate of *Lactobacillus reuteri*.
The *Lactobacillus sakei* GMNL-76 and *Lactobacillus reuteri* GMNL-89 were respectively deposited in the Biosource Collection and Research Center (BCRC) of the Food Industry Research and Development Institute (FIRDI) (331 Shih-Pin Road, Hsinchu city 300, Taiwan, R.O.C.) on Jun. 14, 2007, and Nov. 14, 2006, under accession numbers BCRC 910355 and BCRC 910340, respectively. These isolates were also deposited in the China Center for Type Culture Collection (CCTCC) (Wuhan University, Wuhan, 430072, People's Republic of China) under the Budapest Treaty on Nov. 19, 2007 under accession numbers CCTCC M 207153 and CCTCC M 207154, respectively.

Example 5

Evaluation of Abilities of *Lactobacillus* Isolates GMNL-76 and GMNL-89 and Known Strains in Stimulating IL-10 Secretion by Rat Spleen Monocytes To demonstrate that the ability to stimulate monocytes to secrete more IL-10 is a bioactivity specific to *Lactobacillus* isolates GMNL-76 and GMNL-89, these isolates were compared with seven known strains (i.e., *Lactobacillus sakei* BCRC 12933 and BCRC 17500, and *Lactobacillus reuteri* BCRC 14625, BCRC 16090, BCRC 16091, BCRC 17476, and BCRC 17478 purchased from FIRDI) in the following experiment.
Materials and Methods:
The evaluation of IL-10 concentration was essentially based on the operating procedure described in Item C of Example 1, and *Lactobacillus* isolates GMNL-76 and GMNL-89 according to this invention and the seven known strains were used to conduct the experiment. The $OD_{405}$ values thus obtained were subsequently converted to concentrations expressed in pg/mL based on a correlation curve previously prepared by plotting different known concentrations of IL-10 standards versus their $OD_{405}$ values. The experiment for each strain was repeated twice, and the experimental data was expressed in mean±standard deviation.
Result:
The following Table 7 shows the results of IL-10 secretion by rat spleen monocytes stimulated by GMNL-76, GMNL-89, and the seven known strains.

TABLE 7

| Strain number | IL-10 (pg/mL) |
|---|---|
| GMNL-76 | 274.164 ± 9.173 |
| GMNL-89 | 311.07 ± 11.79 |
| BCRC 14625 | 231.52 ± 11.78 |
| BCRC 16090 | 155.35 ± 12.81 |
| BCRC 16091 | 160.874 ± 6.13 |
| BCRC 17476 | 292.86 ± 24.97 |
| BCRC 17478 | 232.269 ± 16.385 |
| BCRC 12933 | 250.996 ± 3.672 |
| BCRC 17500 | 266.958 ± 12.759 |

It is evident from Table 7 that, of all the tested strains, *Lactobacillus* isolate GMNL-89 of the invention and the known strain BCRC 17476 have the highest abilities to stimulate rat spleen monocytes to secrete IL-10, with GMNL-76 second thereto. The experiment results shown in Table 7 also demonstrate that *Lactobacillus* isolates GMNL-89 and GMNL-76 of this invention are different from the other known strains belonging to the same species.

Example 6

Acid Tolerance Test and Bile Salt Tolerance Test on *Lactobacillus* GMNL-76 and GMNL-89

To test the abilities of *Lactobacillus* GMNL-76 and GMNL-89 to survive the harsh environment of the human digestive tract after being ingested, an experiment to simulate the digestive process in the human digestive tract was conducted.
Materials:
1. MRS Broth (pH=3)
   55 g of MRS powder (BD, Cat. No. 288130) was dissolved in 1 L of RO water and sufficiently mixed, followed by adjustment of the pH value to 3 using 1 M HCl, and sterilization at 121° C. for 15 minutes. The resultant broth was put aside for subsequent use after cooling.

2. MRS Broth Medium Containing 0.2% (w/v) of Ox Gall:

55 g of MRS powder was dissolved in 1 L of RO water and sufficiently mixed so as to obtain a MRS broth medium, followed by sterilization at 121° C. for 15 minutes. When the temperature of the MRS broth medium dropped to about 45° C., 2 g of ox gall powder (Sigma) was added and sufficiently mixed so as to obtain a MRS broth medium containing 0.2% (w/v) of ox gall, which was subsequently filtered using a filter with a porosity of 0.45 μm.

3. MRS Agar Plate:

55 g of MRS powder was dissolved in 1 L of RO water. 15 g of agarose powder was added after the MRS powder was completely dissolved. The mixture thus formed was subsequently poured into a 1-L serum flask and was subjected to sterilization at 121° C. for 15 minutes. When the temperature of the mixture dropped to 45° C., about 15 to 20 mL of the mixture was added to each petri dish under sterile operating conditions. The resultant mixture was allowed to cool and coagulate for subsequent use.

Methods:

A. Acid Tolerance Test:

27 mL of the MRS broth medium (pH=3) was inoculated with 3 mL of the test bacterial solution obtained in Item A of Example 1 and was sufficiently mixed therewith, followed by incubation at 37° C. for 3 hours. Thereafter, 1 mL of the culture was taken and was subjected to serial dilution with sterile water, followed by a spread plate procedure ($10^{-9} \sim 10^{-1}$). Thereafter, the number of surviving bacteria was counted.

B. Bile Salt Tolerance Test:

After completion of the acid tolerance test, the remaining 29 mL of the culture was centrifuged at 4,000 rpm for 15 minutes. The supernatant was removed, and 30 mL of sterile water was added to suspend the bacteria. Subsequently, centrifugation at 4,000 rpm was performed for 15 minutes, and the supernatant was removed, thereby removing the acidic MRS broth medium. Next, 30 mL of MRS broth medium containing 0.2% (w/v) of ox gall was used to disperse the bacteria, followed by incubation of the culture thus formed at 37° C. for 3 hours. Thereafter, 1 mL of the culture was taken and subjected to serial dilution using sterile water, and a spread plate procedure ($10^{-9} \sim 10^{-1}$) was performed. The number of surviving bacteria was counted.

Result:

The growth of Lactobacillus GMNL-76 and GMNL-89 after undergoing the simulated human digestive process is shown in the following table 8.

TABLE 8

| Lactobacillus isolate number | Cell concentration (CFU/mL) of bacterial solution | | |
|---|---|---|---|
| | Before processing | Cultured in MRS broth medium (pH = 3) for 3 hours | Cultured in MRS broth medium containing 0.2% ox gall for 3 hours* |
| GMNL-76 | $3.76 \times 10^8$ | $1.83 \times 10^5$ | $6.3 \times 10^5$ |
| GMNL-89 | $1.9 \times 10^9$ | $6.83 \times 10^8$ | $1.2 \times 10^9$ |

*Isolate was previously cultured in MRS broth medium (pH = 3) for three hours.

It is apparent from Table 8 that, after the two Lactobacillus isolates of this invention were cultured in MRS broth medium (pH=3) for three hours, the viable bacteria count for Lactobacillus GMNL-76 is $1.83 \times 10^5$ CFU/mL after processing. As for Lactobacillus GMNL-89, the viable bacterial cell count is $6.83 \times 10^8$ CFU/mL. After the two Lactobacillus isolates were cultured in MRS broth medium containing 0.2% ox gall for three additional hours, the viable bacterial cell count did not drop, showing that the two Lactobacillus isolates had excellent survival rate in the MRS broth medium containing 0.2% ox gall. Such results indicate that Lactobacillus GMNL-76 and GMNL-89 were able to overcome the environmental pressure posed by the human digestive tract, and could reach and colonize the intestine(s) after ingestion.

All patents and literature references cited in the present specification are hereby incorporated thereinto by reference in their entirety. In case of conflict, the present description, including definitions, shall prevail.

While the invention has been described with reference to the above specific embodiments, it is apparent that numerous modifications and variations can be made without departing from the scope and spirit of this invention. It is therefore intended that this invention be limited only as indicated by the appended claims.

What is claimed is:

1. A biologically pure culture of a *Lactobacillus sakei* strain designated
GMNL-76, deposited in China Center for Type Culture Collection (CCTCC) under accession number CCTCC M 207153.

2. A pharmaceutical composition comprising the *Lactobacillus sakei* strain of claim 1.

3. The pharmaceutical composition of claim 2, which is manufactured in an oral dosage form.

4. A food product comprising an edible material and the *Lactobacillus sakei* strain of claim 1.

5. A biologically pure culture of a *Lactobacillus reuteri* strain designated
GMNL-89, deposited in China Center for Type Culture Collection (CCTCC) under accession number CCTCC M 207154.

6. A pharmaceutical composition comprising the *Lactobacillus reuteri* strain of claim 5.

7. The pharmaceutical composition of claim 6, which is manufactured in an oral dosage form.

8. A food product comprising an edible material and the *Lactobacillus reuteri* strain of claim 5.

* * * * *